United States Patent
Kim et al.

(10) Patent No.: US 8,456,127 B2
(45) Date of Patent: Jun. 4, 2013

(54) METHOD OF OBTAINING IMAGE OF DISC AND APPARATUS FOR DRIVING DISC

(75) Inventors: Jong-cheol Kim, Suwon-si (KR); Chung-ung Kim, Yongin-si (KR); Ki-ju Lee, Suwon-si (KR); Jong-jin Park, Yonging-si (KR); Dong-hwi Cho, Suwon-si (KR); Su-bong Bae, Suwon-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 578 days.

(21) Appl. No.: 12/707,741

(22) Filed: Feb. 18, 2010

(65) Prior Publication Data

US 2010/0254238 A1   Oct. 7, 2010

(30) Foreign Application Priority Data

Apr. 1, 2009  (KR) .................. 10-2009-0028256

(51) Int. Cl.
*G05B 1/02* (2006.01)
*G05D 1/02* (2006.01)

(52) U.S. Cl.
CPC .................. *G05D 1/0206* (2013.01)
USPC ........... 318/647; 318/648; 318/649; 318/650; 318/651; 318/652

(58) Field of Classification Search
CPC .................................. G05D 1/0206
USPC .......................... 318/647, 648–653
See application file for complete search history.

(56) References Cited

U.S. PATENT DOCUMENTS

| | | | | |
|---|---|---|---|---|
| 5,448,435 | A * | 9/1995 | Nakazawa et al. | 360/256.3 |
| 7,042,128 | B2 * | 5/2006 | Zepp et al. | 310/191 |
| 7,275,303 | B1 * | 10/2007 | O'Day | 29/603.04 |
| 7,990,819 | B2 * | 8/2011 | Wakabayashi et al. | 369/44.37 |
| 2002/0076354 | A1 | 6/2002 | Cohen | |

FOREIGN PATENT DOCUMENTS

| | | |
|---|---|---|
| KR | 10-2002-0047503 | 6/2002 |
| KR | 10-2008-0003404 | 1/2008 |

\* cited by examiner

*Primary Examiner* — Walter Benson
*Assistant Examiner* — David Luo
(74) *Attorney, Agent, or Firm* — Staas & Halsey LLP

(57) ABSTRACT

Provided is a method of obtaining an image of a disc, in which the method obtains an image of an analysis or test result object of a disc by minimizing a difference between the positionings of a magnet of the disc and a magnet of a feeding unit, and an apparatus for driving a disc, wherein the apparatus performs the method. The method includes: fixing a positioning of a disc by using magnetic attraction between a first magnet installed on the disc and a second magnet installed on a feeding unit; minimizing a difference between the positionings of the first and second magnets; and obtaining an image of an analysis or test result object of the disc.

15 Claims, 8 Drawing Sheets

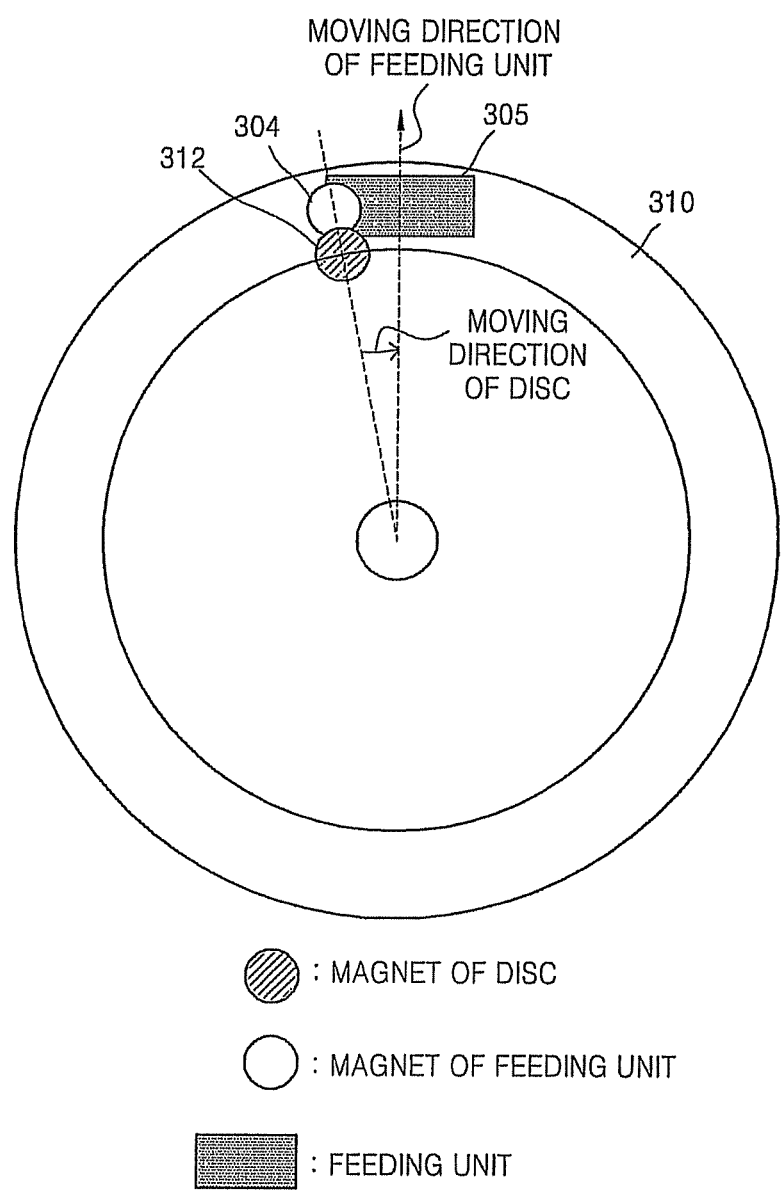

METHOD OF OBTAINING IMAGE OF DISC AND APPARATUS FOR DRIVING DISC

CROSS-REFERENCE TO RELATED APPLICATIONS

This application claims the benefit of Korean Patent Application No. 10-2009-0028256, filed on Apr. 1, 2009, in the Korean Intellectual Property Office, the disclosure of which is incorporated herein in its entirety by reference.

BACKGROUND

1. Field

The inventive concept relates to obtaining an image of a disc, and more particularly, to a method of obtaining an image of an analysis or test result of a disc, and an apparatus for driving a disc, wherein the apparatus includes a disc and a feeding unit each having a magnet and the apparatus performs the method.

2. Description of Related Art

A disc having a magnet may be a bio disc. A bio disc may be a digital bio disc on which a lab on a chip, which includes one of various diagnosis analyzing apparatuses, a nucleic acid hybrid analyzing apparatus, or an immunological verifying apparatus for a sample injected into the bio disc, is disposed.

Such a bio disc (hereinafter, referred to as a disc) includes an analysis result object or a test result object, such as a piece of reaction-paper, that shows an analysis or test result. Magnets included in each of a disc and a feeding unit may be used to fix the positioning of the disc where an image obtainer, such as an image sensor or a camera unit, can recognize the analysis or test result object, when an image of the analysis or test result object is to be obtained.

However, a difference between positionings of the magnets included in each of the disc and the feeding unit can occur.

SUMMARY

Additional aspects and/or advantages will be set forth in part in the description which follows and, in part, will be apparent from the description, or may be learned by practice of the invention.

The inventive concept provides a method of obtaining an image of a disc, where the method obtains an image of an analysis or test result object of a disc by minimizing a difference between the positioning of a magnet of the disc and the positioning of a magnet of a feeding unit, and an apparatus for driving a disc, wherein the apparatus performs the method.

According to an aspect of the inventive concept, a method of obtaining an image of a disc, the method including: fixing a positioning of a disc by using magnetic attraction between a first magnet installed to or on the disc and a second magnet installed to or on a feeding unit; minimizing a difference between positionings of the first and second magnets; and obtaining an image of an analysis or test result object of the disc is provided.

In the minimizing of the difference, the difference between the positionings may be minimized by moving the feeding unit in a direction from an outer circumference of the disc to an inner circumference of the disc at least once. The minimizing of the difference may include further moving the feeding unit in a direction from the inner circumference to the outer circumference at least once.

In the minimizing of the difference, the difference between the positionings may be minimized by moving the feeding unit in a direction from an outer circumference of the disc to an inner circumference of the disc and in a direction from the inner circumference to the outer circumference a plurality of times.

A moving speed of the feeding unit may be a speed that the disc is rotated as the first magnet is affected by a magnetic force of the second magnet.

According to another aspect, there is provided an apparatus for driving a disc, the apparatus including: a turntable on which the disc having a first magnet is mounted; a rotation motor that rotates the turntable; a feeding unit that has a second magnet; a feeding motor that transfers the feeding unit; an image obtainer that obtains an image of an analysis or test result object of the disc; a controller that controls the feeding motor so as to minimize a difference between the positionings of the first and second magnets, when fixing a positioning of the disc using magnetic attraction between the first and second magnets, after analyzing or testing on a sample by the disc, wherein the sample is a sample injected into the disc.

The controller may minimize the difference by controlling the feeding motor to move in a direction from an outer circumference of the disc to an inner circumference of the disc at least once.

The controller may minimize the difference by controlling the feeding motor to further move in a direction from the inner circumference to the outer circumference at least once.

The controller may control the feeding motor so as to minimize the difference by moving the feeding unit in a direction from an outer circumference of the disc to an inner circumference of the disc and in a direction from the inner circumference to the outer circumference a plurality of times.

The controller may control the feeding motor so that the feeding unit moves at a speed that rotates the disc, as the first magnet is affected by a magnetic force of the second magnet.

BRIEF DESCRIPTION OF THE DRAWINGS

These and/or other aspects and advantages will become apparent and more readily appreciated from the following description of the embodiments, taken in conjunction with the accompanying drawings of which:

FIGS. 4A and 4B are diagrams for describing a relationship between a moving direction of a feeding unit and a moving direction of a disc.

DETAILED DESCRIPTION OF EMBODIMENTS

Figure 1:
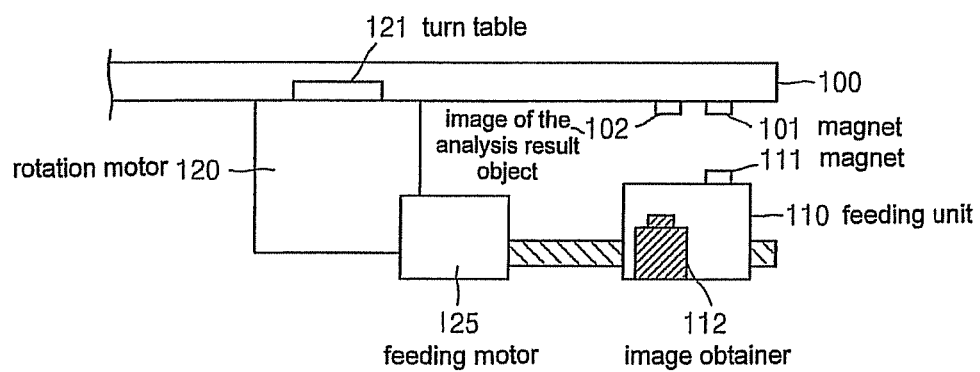
FIG. 1 is a diagram for describing a relationship between a magnet of a disc installed on a turntable, a magnet of a feeding unit, and an image obtainer, when an analysis or test result object of the disc is obtained.

Reference will now be made in detail to the embodiments, examples of which are illustrated in the accompanying drawings, wherein like reference numerals refer to the like elements throughout. The embodiments are described below to explain the present invention by referring to the figures.

Hereinafter, the inventive concept will be described in detail by explaining exemplary embodiments with reference to the attached drawings.

FIG. 1 is a diagram for describing a relationship between a magnet 101 of a disc 100 installed on a turntable 121, a magnet 111 of a feeding unit 110, and an image obtainer 112, when an image of an analysis or test result object (hereinafter, abbreviated to an analysis result object) 102 of the disc 100 is to be obtained. Referring to FIG. 1, when the image of the analysis result object 102, installed on the disc 100, is to be obtained after completing an analysis or a test of the disc 100 installed on the turntable 121 of a rotation motor 120, the positioning of the disc 100 is fixed by a magnetic attraction between the magnet 101, which is installed below the disc 100, and by the magnet 111, which is installed on the feeding unit 110. Here, the positioning of the disc 100 is a positioning where the image obtainer 112 is able to recognize the analysis result object 102. Accordingly, the magnet 101 and the magnet 111 have opposite polarities. A feeding motor 125 controls the feeding unit 110 to move along a radial direction of the disc 100.

Figure 2A:
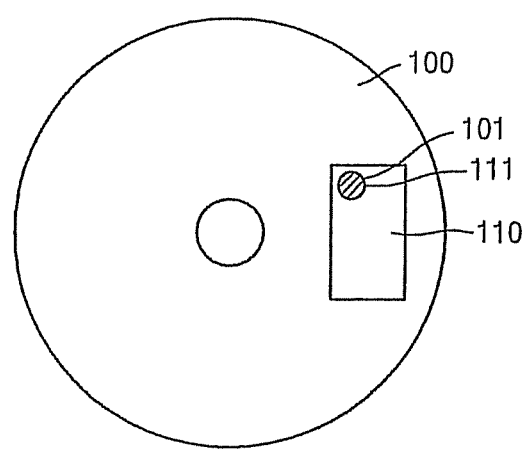
FIGS. 2A through 2C are conceptual diagrams for describing a difference between positionings of a magnet of a disc and a magnet of a feeding unit, viewed from a top surface of the disc.

When the positioning of the magnet 101 of the disc 100 and the positioning of the magnet 111 of the feeding unit 110 correspond to each other as shown in FIG. 2A, an image of the analysis result object 102 obtained by the image obtainer 112 does not have slope or alignment deviation.

Figure 2B:
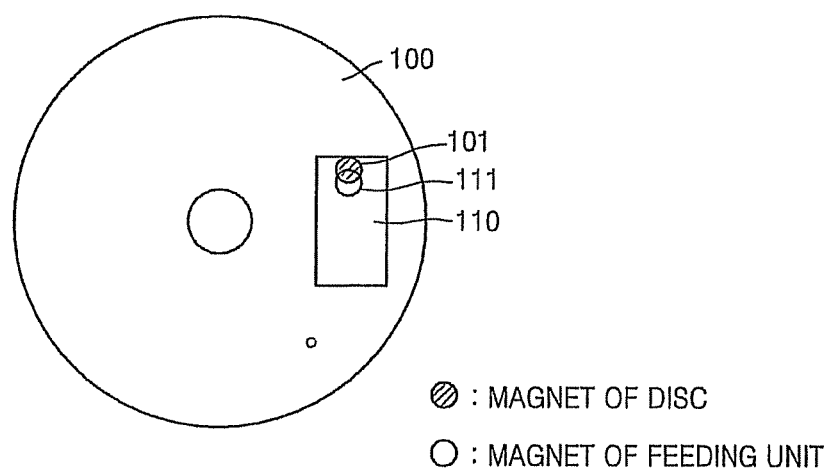
Figure 2C:
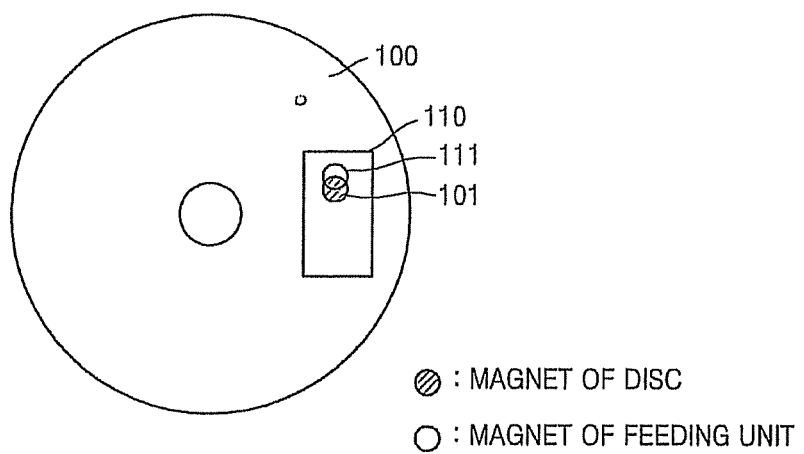

However, since characteristics of the rotation motor 120 and magnetic force between the magnet 101 and the magnet 111 are not always consistent, the positioning of the magnet 101 and the positioning of the magnet 111 may not correspond to or align with each other, such as shown in FIGS. 2B and 2C.

When the positioning of the magnet 101 and the positioning of the magnet 111 do not correspond to each other, an image of the analysis result object 102 obtained by the image obtainer 112 has slope deviation. In other words, when the positioning of the magnet 101 differs from the positioning of the magnet 111, the image of the analysis result object 102 obtained by the image obtainer 112 has slope deviation. As such, when an image obtained by the image obtainer 112 has slope deviation, it is hard to obtain an accurate image of the analysis result object 102.

FIGS. 2A through 2C are conceptual diagrams for describing a difference between the positionings of the magnet 101 of the disc 100 and the magnet 111 of the feeding unit 110, wherein a top surface of the disc 100 is shown. FIG. 2A illustrates a case when a difference does not exist between the magnets 101 and 111, and FIGS. 2B and 2C illustrate cases when an alignment difference exists between the magnets 101 and 111.

Figure 3:
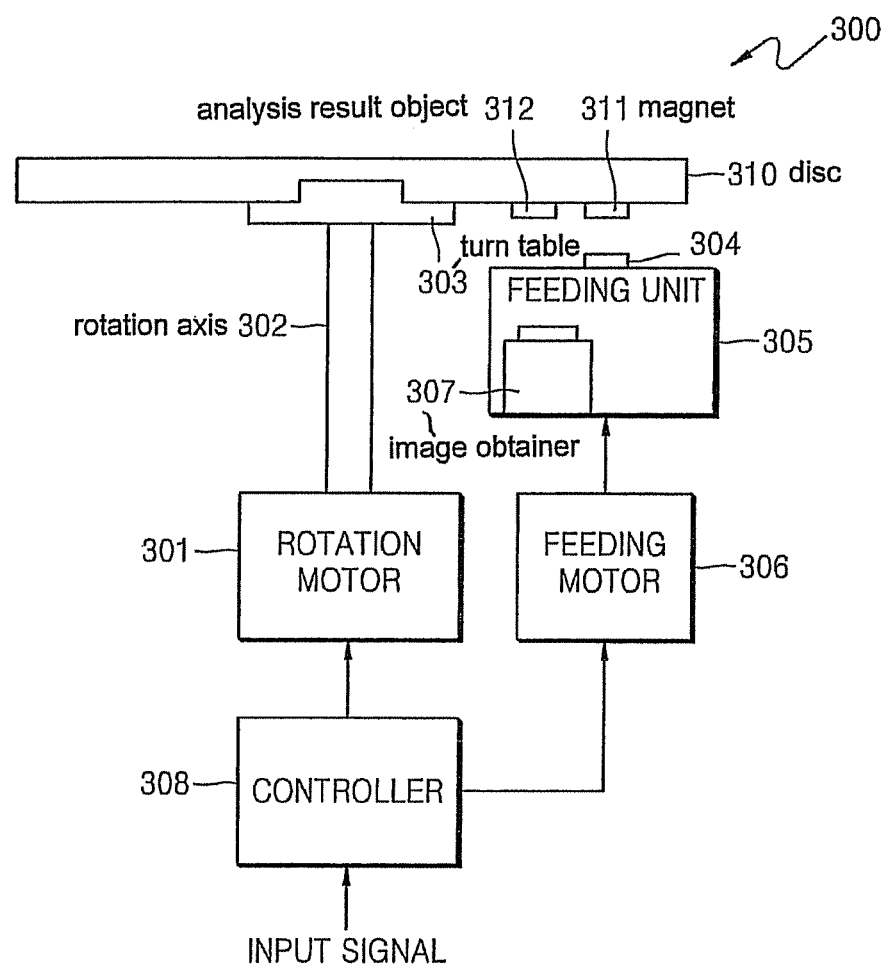
FIG. 3 is a functional block diagram of an apparatus for driving a disc, according to an embodiment.

FIG. 3 is a functional block diagram of an apparatus 300 for driving a disc 310, according to an embodiment. Referring to FIG. 3, the apparatus 300 includes a rotation motor 301, a rotation axis 302, a turntable 303, a feeding unit 305 installed with a magnet 304, a feeding motor 306, an image obtainer 307, and a controller 308.

A magnet 311 and an analysis or test result object (hereinafter, abbreviated to analysis result object) 312 are installed on the disc 310. The magnet 311 may be a permanent magnet. The analysis result object 312 may be a piece of reaction-paper or an assay site. The analysis result object 312 may show a result of analyzing or testing the disc 310. The disc 310 may be a non-optical bio disc or an optical bio disc. The disc 310 analyzes or tests a sample injected into the disc 310.

When the disc 310 is mounted on the turntable 303, which is installed on the rotation axis 302, the controller 308 controls the rotation motor 301 to rotate the disc 310 so that the disc 310 performs analysis or test. The rotation motor 301 may be a spindle motor.

After analyzing or testing by the disc 310, the controller 308 controls the rotation motor 301 to stop the rotating of the disc 310. Here, the controller 308 fixes the positioning of the disc 310 to obtain an image of the analysis result object 312, which is installed on the disc 310, after the analysis or test. To fix the positioning of the disc 310, the controller 308 controls the feeding motor 306 to move the feeding unit 305 so that the positioning of the magnet 304 of the feeding unit 305 and the positioning of the magnet 311 of the disc 310 correspond to or align with each other along a radial direction of the disc.

The feeding motor 306 may control the feeding unit 305 to move along a radial direction of the disc 310. The feeding unit 305 may be a slider or a sled. Since the feeding unit 305 may include a bio optical pickup module, the feeding unit 305 may be a bio optical pickup unit. The magnet 304 is oriented to have a polarity opposite to that of the magnet 311 facing the magnet 304, and is disposed in such a position that the analysis result object 312 installed on the disc 310, by a magnetic attraction with the magnet 311, is recognized by the image obtainer 307. The magnet 304 may be a permanent magnet.

The controller 308 controls the feeding motor 306 to drive the feeding unit 305. The feeding motor 306 may be a slider motor or a sled motor.

The image obtainer 307 includes an image sensor, a camera unit, or a camera module, and obtains an image of the analysis result object 312 of the disc 310. Accordingly, the image obtainer 307 may be installed on the feeding unit 305, but instead, may be fixed in a positioning independent from the feeding unit 305. In order for the image obtainer 307 to obtain an image of the analysis result object 312 of the disc 310, the apparatus 300 may include a lighting unit (not shown) using a device such as a light emitting diode (LED) (not shown). The lighting unit may be disposed adjacent to the image obtainer 307. For example, the LED may be disposed adjacent to the image obtainer 307, or the lighting unit may be disposed on a case surface of the apparatus 300 facing the top of the disc 310.

When the image obtainer 307 includes an image sensor, the image obtainer 307 may be a line image sensor that senses the amount of light on a pixel unit.

The controller 308 may control the feeding motor 306 to minimize a radial alignment difference between positionings of the magnet 304 and the magnet 311, before the image obtainer 307 is to obtain an image of the analysis result object 312 and after fixing the positioning of the disc.

In other words, in order to minimize the difference, the controller 308 may control the feeding motor 306 to move the feeding unit 305 in a direction from an outer circumference to an inner circumference of the disc 310 at least once. Alternatively, the controller 308 may control the feeding motor 306 to move the feeding unit 305 in a direction from an outer circumference to an inner circumference of the disc 310 once, and then further move the feeding unit 305 in a direction from the inner circumference to an outer circumference at least once. Alternatively, the controller 308 may control the feeding motor 306 to move the feeding unit 305 in a direction from an inner circumference to an outer circumference of the disc 310 once, and then in a direction from the outer circumference to an inner circumference of the disc 310 once.

Alternatively, the controller 308 may control the feeding motor 306 to move the feeding unit 305 in a direction from an outer circumference to an inner circumference and in a direction from an inner circumference to an outer circumference a plurality of times.

As described above, a difference between positionings of a magnet of a disc and a magnet of a feeding unit is minimized when obtaining an image of analysis or test result object of the disc, and thus slope deviation of the obtained image is minimized. Accordingly, an apparatus of driving a disc that has high reliability for an image analysis result can be provided.

Figure 4A:
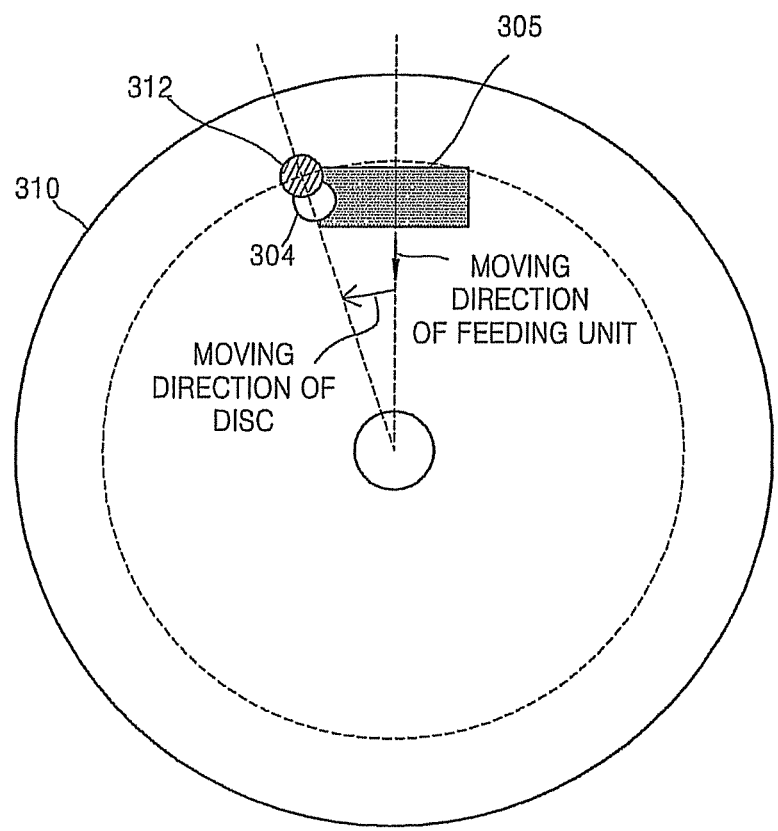

FIGS. 4A and 4B are diagrams for describing a relationship between a moving direction of the feeding unit 305 and a moving direction of the disc 310. FIG. 4A illustrates a case where the disc 310 rotates counterclockwise as the magnet 311 of the disc 310 is affected by a magnetic force of the magnet 304 of the feeding unit 305, when the feeding unit 305 moves in a direction from an outer circumference to an inner circumference of the disc 310. FIG. 4B illustrates a case where the disc rotates clockwise as the magnet 311 is affected by the magnetic force of the magnet 304, when the feeding unit 305 moves in a direction from the inner circumference to the outer circumference of the disc 310. The controller 308 controls the feeding motor 306 to minimize the difference between positionings of the magnets 311 and 304 based on the moving direction of the feeding unit 305 and the rotation direction of the disc 310. Here, the controller 308 controls the feeding motor 306 to move the feeding unit 305 at a speed that rotates the disc 310 as the magnet 311 of the disc 310 is affected by a magnetic force to the magnet 304 of the feeding unit 305.

After minimizing the difference between the positionings of the magnets 311 and 304, the controller 308 controls the image obtainer 307 to obtain an image of the analysis result object 312 of the disc 310. The obtained image may be output via an output unit (not shown) connected to the apparatus 300 of FIG. 3. The output unit transmits or displays the obtained image, and may be an Internet interface unit, a computer system, or a display unit. An analysis result of the disc 310 is determined based on the image output via the output unit.

As described above, by minimizing the difference between positionings of the magnets 311 and 304 when obtaining the image of the analysis result object 312 of the disc 310, slope deviation of the image of the analysis result object 312 is minimized. Accordingly, the apparatus 300 having high reliability on an image analysis result can be provided.

Figure 5:
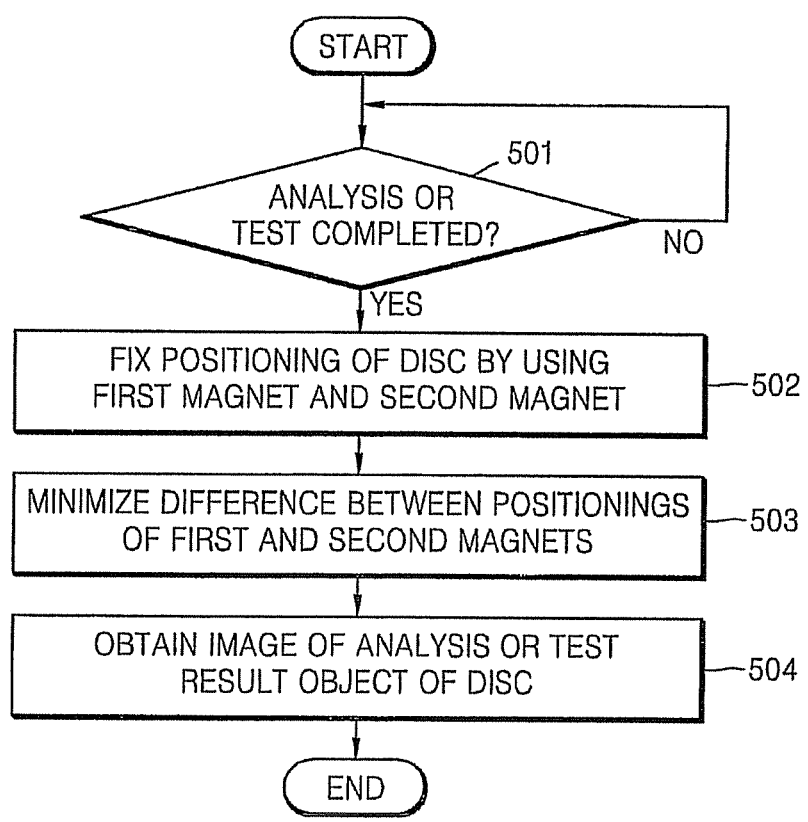
FIG. 5 is a flowchart illustrating a method of obtaining an image of a disc, according to an embodiment.

FIG. 5 is a flowchart illustrating a method of obtaining an image of a disc, according to an embodiment. The image of the disc is an analysis or test result image of the disc, and is obtained based on an analysis or test result object installed on the disc. The method will now be described with reference to FIGS. 3 and 5.

Referring to FIG. 5, it is determined whether an analysis or test on a sample by a disc is completed in operation 501. The sample is a sample injected into the disc 310. If the analysis or test by the disc 310 is completed, the controller 308 fixes a positioning of the disc 310 by using a first magnet and a second magnet. Here, the first magnet is the magnet 311 of the disc 310 and the second magnet is the magnet 304 of the feeding unit 305. The positioning of the disc 310 is a positioning where the image obtainer 307 can recognize the analysis result object 312 installed on the disc 310.

Next, in operation 503, the controller 308 minimizes a difference between positionings of the magnets 311 and 304. In order to minimize the difference, the controller 308 may control the feeding motor 306 to move the feeding unit 305 in a direction from an outer circumference of the disc 310 to an inner circumference of the disc 310 at least once. Alternatively, the controller 308 may control the feeding motor 306 to move the feeding unit 305 in a direction from the outer circumference to the inner circumference once, and then in a direction from the inner circumference to the outer circumference at least once. Alternatively, the controller 308 may control the feeding motor 306 to move the feeding unit 305 in a direction from the outer circumference to the inner circumference and in a direction from the inner circumference to the outer circumference a plurality of times. Here, the controller 308 controls the feeding motor 306 to move the feeding unit 305 at a speed that rotates the disc 310 as shown in FIGS. 4A and 4B as the magnet 311 is affected by magnetic force to the magnet 304.

After minimizing the difference between positionings of the magnets 311 and 304, the controller 308 controls the image obtainer 307 to obtain an image of the analysis result object 312 of the disc 310 in operation 504. The image of the analysis result object 312 is an analysis result on the sample injected into the disc 310.

In the method, operations 502 through 504 may be performed according to an image obtaining request of a user on the disc 310 that is completed the analysis or test on the sample.

The embodiments can be implemented as a method, an apparatus, and a system. When the embodiments are implemented in software, its component elements are code segments that execute necessary operations. Programs or code segments can be stored in processor readable media. The processor readable medium can be any medium that can store or transmit data. Examples of the processor readable medium include electronic circuits, semiconductor memory devices, ROMs, flash memories, erasable ROMs (EROMs), floppy discs, optical discs, hard discs, optical fibers, radio frequency (RF) networks, etc.

Although a few embodiments have been shown and described, it would be appreciated by those skilled in the art that changes may be made in these embodiments without departing from the principles and spirit of the invention, the scope of which is defined in the claims and their equivalents.

What is claimed is:

1. A method of obtaining an image for test result object of a disc, the method comprising:
   fixing a positioning of a disc by using magnetic attraction creating an alignment between a first magnet installed on the disc and a second magnet installed on a feeding unit;
   minimizing an alignment difference of the first and second magnets, wherein minimizing the difference is performed by moving the feeding unit in a direction from an outer circumference of the disc to an inner circumference of the disc and in a direction from the inner circumference to the outer circumference one or more times; and
   obtaining an image of an analysis or test result object on the disc using an image obtaining unit.

2. The method of claim 1, wherein a moving speed of the feeding unit is a speed that the disc is rotated as the first magnet is affected by magnetic force to the second magnet.

3. The method of claim 1, wherein the difference comprises a radial alignment difference and the radial alignment difference is minimized.

4. The method of claim 1, wherein the disc is a bio disc, and wherein the analysis or test result object comprises a piece of reaction paper.

5. An apparatus for driving a disc, the apparatus comprising:
   a turntable on which the disc having a first magnetic material is attached;
   a rotation motor to rotate the turntable;
   a feeding unit having a second magnet attached thereon;
   a feeding motor that transfers the feeding unit;
   an image obtainer that obtains an image of an analysis or test result object on the disc; and a controller that controls the feeding motor to minimize misalignment between the first magnetic material and the second magnet, wherein minimizing the misalignment is performed by moving the feeding unit in a direction from an outer circumference of the disc to an inner circumference of the disc and in a direction from the inner circumference to the outer circumference one or more times;

wherein after the minimizing the misalignment, the image of an analysis or test result object on the disc is configured to be obtained with the image obtainer.

6. The apparatus of claim 5, wherein the controller controls the feeding motor so that the feeding unit moves at a speed that rotates the disc, as the first magnet is affected by a magnetic force of the second magnet.

7. The method of claim 5, wherein the image obtainer is coupled to the feeding unit so that when the feeding unit moves, the image obtainer moves together with the feeding unit.

8. The method of claim 5, the analysis or test result object is configured to positioned close to a center of the disc rather than the first magnetic material in the radial direction.

9. A method of obtaining an image for a test result object of a disc, the method comprising:

performing a test on a sample provided in the disc mounted on a turntable, wherein the disc comprises a first magnetic material and is configured to be rotated with the turntable;

positioning the disc with a feeding unit located below the disc so that the first magnetic material is configured to be positioned close to a second magnet provided on the feeding unit by using magnetic force between the first magnetic material and the second magnet moving the feeding unit along a radial direction of the disc to minimize an alignment difference between the first magnetic material and the second magnet wherein the moving the feeding unit is performed by moving the feeding unit in a direction from an outer circumference of the disc to a center of the disc and in a direction from the center to the outer circumference one or more times; and obtaining an image of the test result object on the disc using an image obtaining unit.

10. The method of claim 9, wherein, in the minimizing of the difference, the first magnetic material moves clockwise or counterclockwise.

11. The method of claim 9, wherein the image obtaining unit is coupled to the feeding unit so that when the feeding unit moves, the image obtaining unit moves together with the feeding unit.

12. The method of claim 9, the test result object is configured to positioned close to the center of the disc rather than the first magnetic material in the radial direction.

13. The method of claim 9, the test result object comprises a piece of reaction paper.

14. The method of claim 9, the image is configured to be obtained by using an light of a lighting unit disposed adjacent to or opposite to the image obtaining unit.

15. A method of obtaining an image for a test result object of a bio disc, the method comprising:

performing a test on a sample provided in a disc mounted on a turntable, wherein the disc comprises a first magnetic material and is configured to be rotated with the turntable;

positioning the disc with a feeding unit located below the disc so that the first magnetic material is configured to be positioned close to a second magnet provided on the feeding unit by using magnetic force between the first magnetic material and the second magnet;

moving the feeding unit along a radial direction of the disc to minimize an alignment difference between the first magnetic material and the second magnet, wherein the moving the feeding unit is performed by moving the feeding unit in a direction from the center to the outer circumference and in a direction from an outer circumference of the disc to a center of the disc one or more times; and obtaining an image of the test result object on the disc using an image obtaining unit.

* * * * *

UNITED STATES PATENT AND TRADEMARK OFFICE
CERTIFICATE OF CORRECTION

| | | |
|---|---|---|
| PATENT NO. | : 8,456,127 B2 | Page 1 of 1 |
| APPLICATION NO. | : 12/707741 | |
| DATED | : June 4, 2013 | |
| INVENTOR(S) | : Jong-cheol Kim et al. | |

It is certified that error appears in the above-identified patent and that said Letters Patent is hereby corrected as shown below:

On the Title Page
Column 1, Item [75] (Inventors), Line 4, Delete "Yonging-si" and insert -- Yongin-si --, therefor.

In the Claims
Column 7, Line 15, In Claim 7, Delete "method" and insert -- apparatus --, therefor.
Column 7, Line 20, In Claim 7, Delete "method" and insert -- apparatus --, therefor.
Column 7, Line 36, In Claim 9, Delete "magnet" and insert -- magnet, --, therefor.

Signed and Sealed this
Tenth Day of November, 2015

Michelle K. Lee
*Director of the United States Patent and Trademark Office*